May 17, 1949. W. B. CLARKE Plant Pat. 837
LILAC PLANT
Filed Aug. 14, 1947
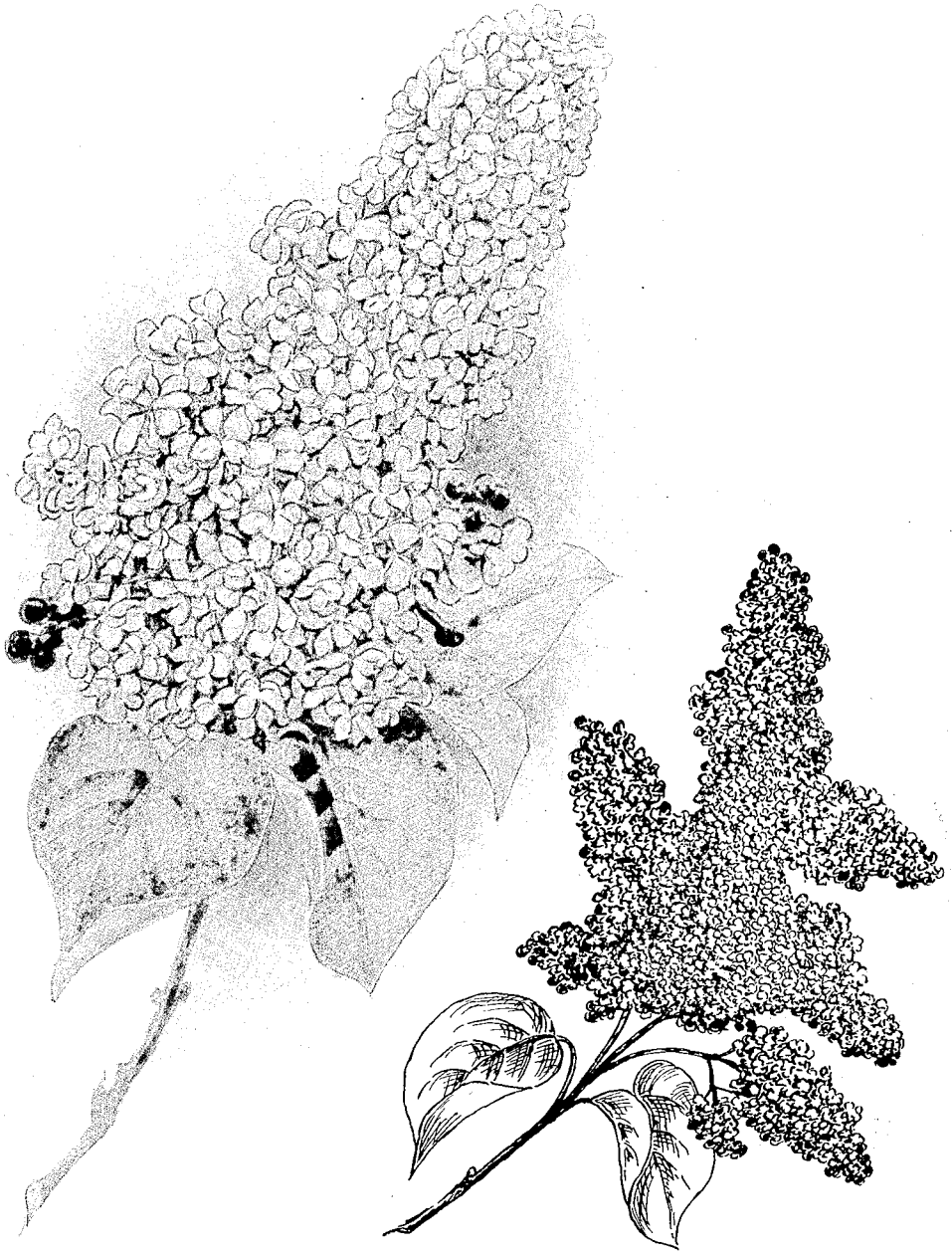
WITNESS
Addison F. Avery
INVENTOR
WALTER BOSWORTH CLARKE,
by Kenneth Kenneth & Snow,
ATTYS.

Patented May 17, 1949

Plant Pat. 837

UNITED STATES PATENT OFFICE

837

LILAC PLANT

Walter Bosworth Clarke, San Jose, Calif., assignor to W. B. Clarke & Co., San Jose, Calif., a partnership Application August 14, 1947, Serial No. 768,584

1 Claim. (Cl. 47—60)

The present discovery relates to a new and distinct variety of *Syringa vulgaris* plant. It is a cross between an unnamed double variety as the seed parent and another unnamed variety as the pollen parent, resulting from extensive breeding efforts.

Its novelty resides primarily in the unique coloring of the flowers; in its abundant floriferousness; in the spacing of the individual double flowers in the uncrowded compound thyrses; in the very dark color of the new growth of bark; in the precociousness of its blooming quite freely on young plants; and in its habit of growing rather wide in proportion to its height which makes it bushy and well shaped. Asexual reproduction of this new variety has shown that the foregoing characteristics come true to form and are established.

The accompanying painting shows, in the left hand view, a single panicle in color and, in the right hand view, a characteristic cluster of blooms.

An important characteristic of this new variety is the marked change in color of the buds from nearly black to a ruddy purple just before opening. The fully developed flowers are double, bluish purple in color and uncrowded in the cluster. Crowding of flowers in the cluster is a fault of many previously known double lilacs. The individual floret is about ⅞ inch in diameter. The clusters are of good size and usually compound. When the clusters are half open, the contrast between the very dark buds and the lighter colored open flowers is very striking. Due to the fact that they are not crowded on their stems, the florets of adjacent panicles tend to intermingle so that when fully open they produce variously formed cloudlike masses of compound blooms.

As this shrub has a long blooming season (from midseason to late) there is a period when the three stages of bloom coloring are simultaneously present; the nearly black buds, the partly open ruddy purple bud petals, and the bluish purple open flowers, which contrast conspicuously with each other and with the very dark coloring of the new bark. It is precocious, blooming quite freely on young plants.

The color designations, according to Maerz & Paul's "A Dictionary of Color," are as follows:

| Item | Plate | Ltr. | No. |
|---|---|---|---|
| Flower: Petals, lightest shade | 41 | D | 4 |
| Shading into | 41 | H | 6 |
| Yellow eye of floret | 11 | L | 6 |
| Buds | 47 | L | 10 |
| Leaves | 21 | L | 6 |

This new variety can best be compared to "Henri Martin," but in my discovery the fully developed bloom is a blend of purple and bluish lilac instead of a purple and lavender coloring.

Having thus disclosed my invention, I claim:

A new and distinct variety of *Syringa vulgaris* plant substantially as shown and described, characterized as to novelty by its habit of prolific flowering; by the bluish purple color of its flowers, the variation of color at definite stages of development from bud to mature bloom; by the spacing of the double flowers in the uncrowded but intermingled compound thyrses; the dark color of the new growth of bark; and its free blooming on young plants.

WALTER BOSWORTH CLARKE.

No references cited.